(12) United States Patent
Chen et al.

(10) Patent No.: US 11,639,349 B2
(45) Date of Patent: May 2, 2023

(54) STEREOSELECTIVE SYNTHESIS OF INTERMEDIATE FOR PREPARATION OF HETEROCYCLIC COMPOUND

(71) Applicants: Tai Gen Biotechnology Co., Ltd., Taipei (TW); TaiGen Biopharmaceuticals Co. (Beijing), Ltd., Beijing (CN)

(72) Inventors: Wen-Chang Chen, Taipei (TW); Han-Pei Hsu, Taipei (TW); Shan-Yen Chou, Taipei (TW); Shih-Chieh Chuang, Taipei (TW); Chi-Feng Yen, Taipei (TW)

(73) Assignees: TaiGen Biotechnology Co., Ltd., Taipei (TW); TaiGen Biopharmaceuticals Co.(Beijing), Ltd., Beijing (CN)

( * ) Notice: Subject to any disclaimer, the term of this patent is extended or adjusted under 35 U.S.C. 154(b) by 196 days.

(21) Appl. No.: 17/331,959

(22) Filed: May 27, 2021

(65) Prior Publication Data
US 2021/0371407 A1 Dec. 2, 2021

Related U.S. Application Data

(60) Provisional application No. 63/030,988, filed on May 28, 2020.

(51) Int. Cl.
*C07D 409/12* (2006.01)
*C07D 471/04* (2006.01)
*C07D 337/12* (2006.01)

(52) U.S. Cl.
CPC ......... *C07D 409/12* (2013.01); *C07D 337/12* (2013.01); *C07D 471/04* (2013.01)

(58) Field of Classification Search
CPC ... C07D 409/12; C07D 337/12; C07D 471/04
See application file for complete search history.

(56) References Cited

FOREIGN PATENT DOCUMENTS

WO WO 2019/144089 * 7/2019 ........... C07D 471/04

* cited by examiner

*Primary Examiner* — Alicia L Otton
(74) *Attorney, Agent, or Firm* — McCarter & English, LLP; Yu Lu; James M. Alburger

(57) ABSTRACT

Provided is a stereoselective synthesis of an intermediate for the preparation of the heterocyclic derivative as a Cap-dependent endonuclease inhibitor. The synthesis process has the advantages of simple operation, higher yield and relatively controllable steroselectivity, such that it is suitable for large-scale production.

15 Claims, No Drawings

STEREOSELECTIVE SYNTHESIS OF INTERMEDIATE FOR PREPARATION OF HETEROCYCLIC COMPOUND

REFERENCE TO RELATED APPLICATION

This application claims the benefit of the filing date of U.S. Provisional Patent Application No. 63/030,988, filed on May 28, 2020, the entire contents of which are incorporated herein by reference.

TECHNICAL FIELD

The present disclosure relates to a stereoselective process for producing a substituted heterocyclic compound. In addition, the present disclosure also relates to an intermediate for preparation of the substituted heterocyclic compound.

BACKGROUND

Cap-dependent endonuclease is an enzyme involving in the inhibition of mRNA synthesis of influenza viruses. Inhibitors of Cap-dependent endonuclease are found to be effectively against influenza virus A and B. Several compounds exhibited potent antiviral activity against influenza virus by inhibiting Cap-dependent endonuclease. In PCT published application, WO2019/144089, novel heterocyclic compounds as potent Cap-dependent endonuclease inhibitors were first disclosed. Also described in WO2019/144089 is a process for preparation of the heterocyclic compounds, comprising using a racemic polycyclic compound containing a sulfur atom as an intermediate. However, synthetic control over the chirality of the heterocyclic compounds is lacking in this prior art.

SUMMARY

The present disclosure provides an intermediate and a synthetic route for preparation of heterocyclic compounds with simple chemical unit operation, higher yield, controllable chirality, and being suitable for industrial production. In some embodiments, the present disclosure also provides a process for preparing heterocyclic compounds by using a stereoselective intermediate.

In at least one embodiment of the present disclosure, an intermediate represented by formula (I) below, or a salt thereof is provided:

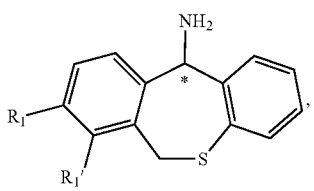

(I)

wherein $R_1$ is halogen; $R_1'$ is halogen; "*" stands for the R-enantiomer or the S-enantiomer.

In at least one embodiment of the present disclosure, an intermediate represented by formula (II) below, or a salt thereof is also provided:

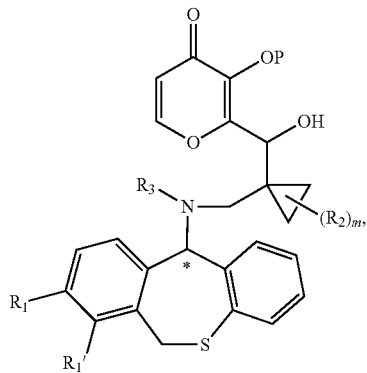

(II)

wherein $R_1$ is halogen; $R_1'$ is halogen; $R_2$ is hydrogen, deuterium, halogen, or $C_1$-$C_6$ alkyl; $R_3$ is hydrogen, NO, or $NH_2$; m is 0, 1, 2, or 3; P is a protecting group; "*" stands for the R-enantiomer, the S-enantiomer, or the racemate.

In at least one embodiment of the present disclosure, a process for preparing the intermediate of formula (I) is provided.

In at least one embodiment of the present disclosure, a process for preparing the intermediate of formula (II) is provided.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

The term "about" will be understood by a person of ordinary skill in the art and will vary to some extent on the context in which it is used. As used herein, when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed processes.

The term "halogen" used herein refers to fluorine, chlorine, bromine, or iodine.

The term "$C_{1-6}$ alkyl" used herein refers to a straight- or branched-chain saturated hydrocarbyl substituent containing 1 to 6 (e.g., 1 to 3, 1 to 4 and 1 to 5) carbon atoms. Examples of $C_{1-6}$ alkyl include methyl, ethyl, n-propyl, isopropyl, n-butyl, isobutyl, sec-butyl, tert-butyl, n-pentyl, and the like.

The term "one or more" used herein refers to either one or a number above one (e.g., 2, 3, 4, 5, 6, 7 or above).

The term "protecting group" used herein refers to a moiety that is formed to render a functional moiety unreactive. The protecting group can be removed so as to restore the functional moiety to its original state. Various protecting groups and protecting reagents, including hydroxy protecting groups, are well known to one of ordinary skill in the art and include compounds that are disclosed in Protective Groups in Organic Synthesis, 4th edition, T. W. Greene and P. G. M. Wilts, John Wiley & Sons, New York, 2006.

The term "salt" used herein refers to an acid or base addition salt of a compound of this disclosure. The "salt" includes, for example, a "pharmaceutically acceptable salt." The term "pharmaceutically acceptable salt" used herein refers to a salt prepared from a pharmaceutically acceptable non-toxic base or acid, including an inorganic or organic base and an inorganic or organic acid. The examples of salts derived from inorganic bases include aluminum, ammonium, calcium, copper, ferric, ferrous, lithium, magnesium, manganese, potassium, sodium, zinc, and the like. The examples of salts derived from pharmaceutically acceptable organic non-toxic bases include salts of primary, secondary, and tertiary amines, naturally occurring substituted amines, cyclic amines, arginine, betaine, caffeine, choline, N,N'-dibenzylethylene-diamine, diethylamine, 2-di ethylamino-ethanol, 2-dimethylaminoethanol, ethanolamine, ethylene-diamine, N-ethyl-morpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like. When the compound employed in the disclosure is basic, salts may be prepared from pharmaceutically acceptable inorganic and organic acids. The examples of such inorganic acids include, but are not limited to hydrochloric acid, hydrobromic acid, sulfuric acid, sulfamic acid, nitric acid, boric acid, phosphoric acid, and the like. The examples of such organic acids include, but are not limited to formic acid, acetic acid, phenylacetic acid, propionic acid, stearic acid, ascorbic acid, maleic acid, hydroxymaleic acid, isethionic acid, succinic acid, valeric acid, fumaric acid, malonic acid, picric acid, pyruvic acid, oxalic acid, glycolic acid, salicylic acid, oleic acid, palmitic acid, lauric acid, malic acid, mandelic acid, citric acid, tartaric acid, a pyranosidyl acid, such as glucuronic acid or galacturonic acid, an amino acid, such as aspartic acid, glutaric acid or glutamic acid, an aromatic acid, such as benzoic acid, 2-acetoxybenzoic acid, naphthoic acid, or cinnamic acid, and the like. It will be understood that, as used herein, references to the compounds of this disclosure are meant to also include the pharmaceutically acceptable salts thereof.

Disclosed first in detail herein is an intermediate of formula (I), represented below, or a salt thereof:

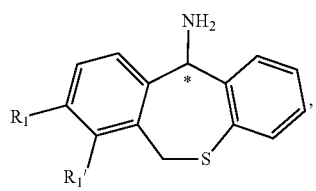

wherein $R_1$ is halogen; $R_1'$ is halogen; "*" stands for the R-enantiomer or the S-enantiomer. In at least one embodiment, $R_1$ is fluorine, and $R_1'$ is fluorine.

In at least one embodiment, the intermediate of formula (I) may be represented by formula (Ia) or formula (Ib):

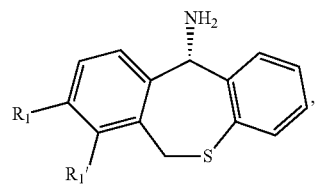

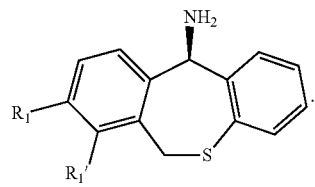

In some embodiments, the intermediate of formula (I) is

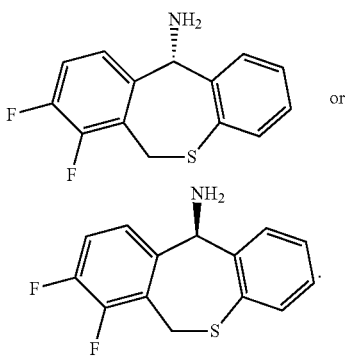

The present disclosure also provides an intermediate represented by formula (II):

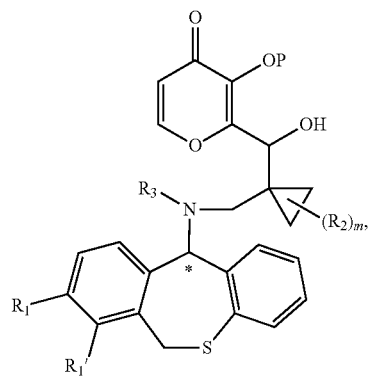

wherein $R_1$ is halogen; $R_1'$ is halogen; $R_2$ is hydrogen, deuterium, halogen, or $C_1$-$C_6$ alkyl; $R_3$ is hydrogen, NO or $NH_2$; m is 0, 1, 2, or 3; P is a protecting group; "*" stands for the R-enantiomer, the S-enantiomer or the racemate. In at least one embodiment, $R_1$ is fluorine, and $R_1'$ is fluorine. In some embodiments, $R_2$ is hydrogen, deuterium, or methyl. In some embodiments, $R_2$ is hydrogen. In some embodiments, $R_3$ is hydrogen or NO. In some embodiments, m is 0. In some embodiments, the examples of the protecting group include, but are not limited to, benzyl (Bn), tertbutyloxycarbonyl (Boc), benzyloxycarbonyl (Cbz), 9-fluorenylmethoxycarbonyl (Fmoc), acetyl (Ac), benzoyl (Bz), trityl and the like.

In at least one embodiment, the intermediate of formula (II) may be represented by formula (IIa) or formula (IIb):

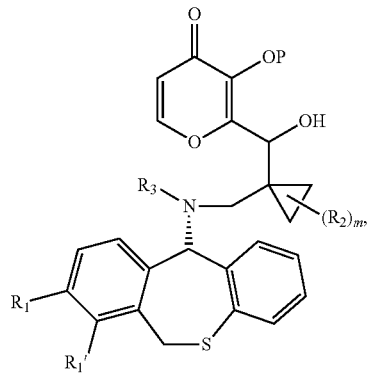

(IIa)

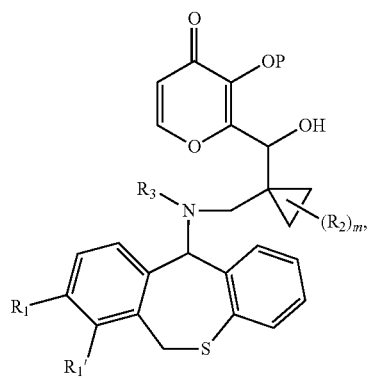

(IIb)

wherein $R_1$, $R_1'$, $R_2$, $R_3$, m, and P are as defined above.

In some embodiments, the intermediate of formula (IIa) may be represented by formula (IIa-1) or formula (IIa-2):

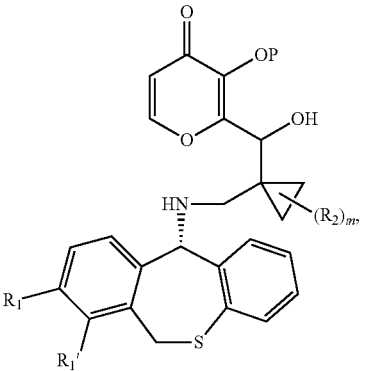

(IIa-1)

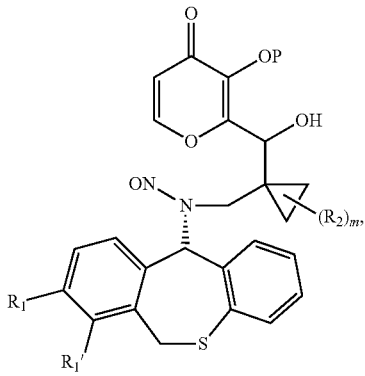

(IIa-2)

wherein $R_1$, $R_1'$, $R_2$, m, and P are as defined above.

In at least one embodiment, the intermediate of formula (IIb) may be represented by formula (IIb-1) or formula (IIb-2):

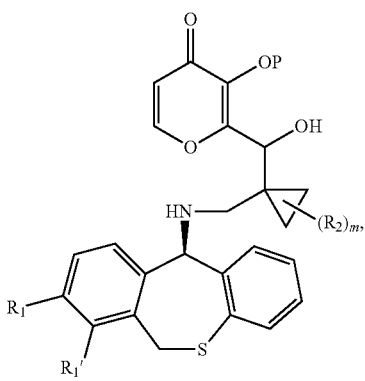

(IIb-1)

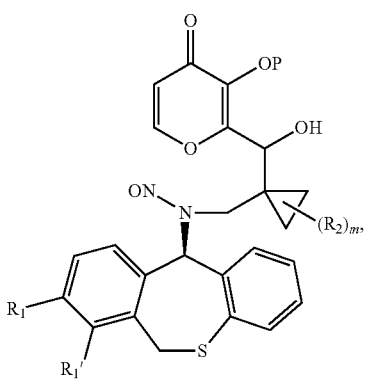

(IIb-2)

wherein $R_1$, $R_1'$, $R_2$, m, and P are as defined above.

In some embodiments, the intermediate of formula (II) is

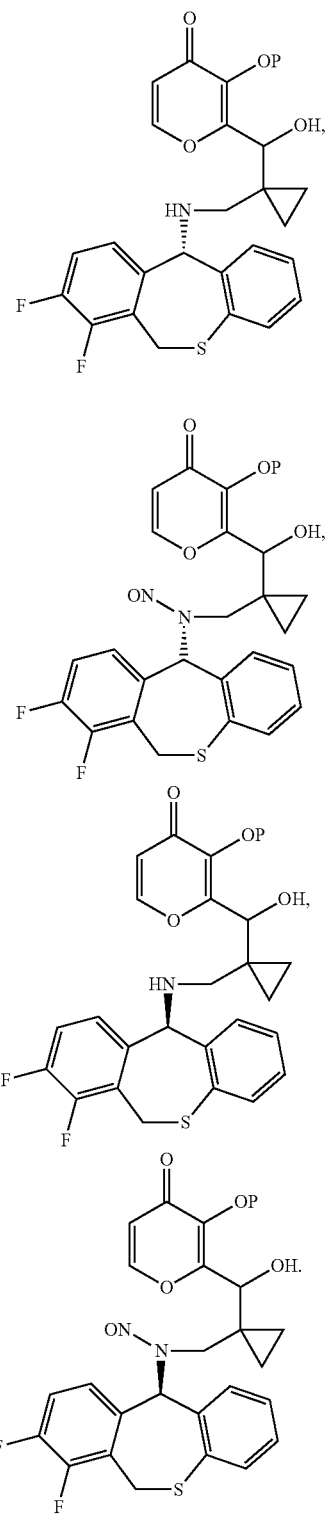

In one aspect of the present disclosure, a process of preparing the compound of formula (II) from the compound of formula (I) is provided.

In at least one embodiment, the present disclosure provides a process of preparing a compound of formula (IIa-1), comprising reacting the compound of formula (I-2) with the compound of formula (Ia) as below:

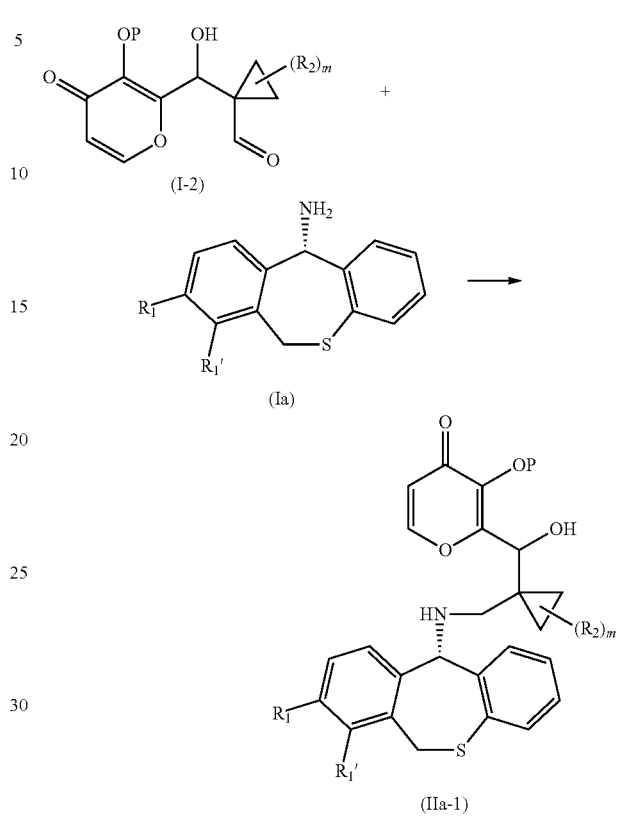

to form the compound of formula (IIa-1), or a salt thereof, in the presence of an inert solvent, a suitable acid and a reducing agent at a temperature between about −20° C. and about 30° C., such as −15° C. to 25° C., −10° C. to 20° C., −5° C. to 15° C., 0° C. to 10° C., 0° C. to 5° C., and 5° C. to 10° C.; wherein $R_1$, $R_1'$, $R_2$, m, and P are as defined above.

In at least one embodiment, the examples of the inert solvent include, but are not limited to, toluene, tetrahydrofuran (THF), methyl tert-butyl ether (MTBE), dichloromethane (DCM), diethyl ether, acetonitrile, dimethylcarbonate, ethylacetate, isopropylacetate, tertbutylacetate, $H_2O$, methanol, isopropanol, ethylene glycol, ethanol, propanol, hexane, heptane and the like, or mixtures thereof. In at least one embodiment, the inert solvent is toluene, THF, MTBE, DCM, diethyl ether, acetonitrile, ethylacetate, isopropylacetate, terbutylacetate, $H_2O$, hexane, heptane or the like, or mixtures thereof.

In at least one embodiment, the examples of the suitable acid include, but are not limited to, acetic acid, sulfuric acid, nitric acid, phosphoric acid, trifluoroacetic acid, maleic acid, fumaric acid, citric acid, oxalic acid, succinic acid, tartaric acid, malic acid, benzoic acid and the like, or mixtures thereof. In at least one embodiment, the suitable acid is acetic acid, citric acid, fumaric acid, maleic acid, malic acid, tartaric acid, benzoic acid, oxalic acid, succinic acid, or the like, or mixtures thereof.

In at least one embodiment, the examples of the reducing agent include, but are not limited to, sodium borohydride ($NaBH_4$), sodium triacetoxyborohydride ($NaBH(OAc)_3$), sodium cyanoborohydride ($NaBH_3CN$), lithium borohydride ($LiBH_4$), potassium borohydride ($KBH_4$) and the like, or mixtures thereof.

In at least one embodiment, the process of preparing a compound of formula (IIa-1) further comprises subjecting the compound of formula (IIa-1) to nitrosation reaction to form the compound of formula (IIa-2):

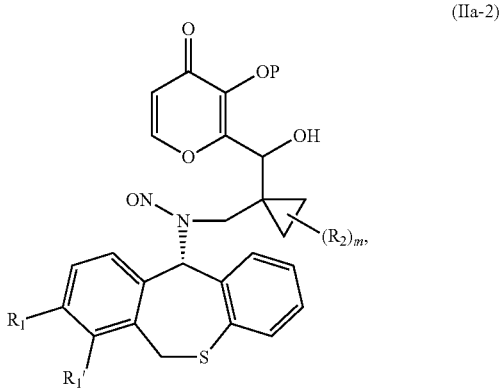

(IIa-2)

or a salt thereof, in the presence of an inert solvent, a suitable acid and a nitrite at a temperature between about −20° C. and about 30° C., such as −15° C. to 25° C., −10° C. to 20° C., −5° C. to 15° C., 0° C. to 10° C., 0° C. to 5° C., and 5° C. to 10° C.; wherein $R_1$, $R_1'$, $R_2$, m, and P are as defined above.

In at least one embodiment, the examples of the inert solvent include, but are not limited to, toluene, THF, MTBE, DCM, diethyl ether, acetonitrile, acetone, dimethylcarbonate, ethylacetate, isopropylacetate, tertbutylacetate, $H_2O$, methanol, isopropanol, ethylene glycol, ethanol, propanol, hexane, heptane and the like, or mixtures thereof. In at least one embodiment, the inert solvent is toluene, THF, MTBE, DCM, diethyl ether, acetonitrile, ethylacetate, isopropylacetate, terbutylacetate, $H_2O$, methanol, isopropanol, ethylene glycol, hexane, heptane or the like, or mixtures thereof.

In at least one embodiment, the examples of the suitable acid include, but are not limited to, acetic acid, sulfuric acid, hydrochloric acid, hydrobromic acid, nitric acid, phosphoric acid, maleic acid, fumaric acid, citric acid, oxalic acid, succinic acid, tartaric acid, malic acid, benzoic acid and the like, or mixtures thereof.

In at least one embodiment, the examples of the nitrite include, but are not limited to, sodium nitrite, potassium nitrite, calcium nitrite, amyl nitrite, isoamyl nitrite, butyl nitrite, and isobutyl nitrite.

In some embodiments, the above process of preparing a compound of formula (IIa-2) further comprises conducting cyclization reaction of the compound of formula (IIa-2) to form the compound of formula (III):

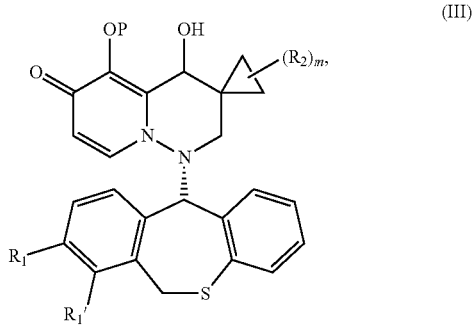

(III)

or a salt thereof, in the presence of an inert solvent, a suitable acid and a catalyst at a temperature between about 30° C. and about 80° C., such as 35° C. to 75° C., 40° C. to 70° C., 45° C. to 65° C., 50° C. to 60° C., 55° C. to 60° C., and 50° C. to 55° C.; wherein $R_1$, $R_1'$, $R_2$, m, and P are as defined above.

In some embodiments, the examples of the inert solvent include, but are not limited to, toluene, THF, MTBE, diethyl ether, acetonitrile, acetone, dimethylcarbonate, ethylacetate, isopropylacetate, tertbutylacetate, $H_2O$, methanol, isopropanol, ethylene glycol, ethanol, propanol, hexane, heptane and the like, or mixtures thereof.

In at least one embodiment, the examples of the suitable acid include, but are not limited to, acetic acid, sulfuric acid, hydrochloric acid, hydrobromic acid, nitric acid, phosphoric acid, trifluoroacetic acid, maleic acid, fumaric acid, citric acid, oxalic acid, succinic acid, tartaric acid, malic acid, benzoic acid and the like, or mixtures thereof.

In at least one embodiment, the examples of the catalyst include, but are not limited to, zinc, iron, manganese, copper, nickel, cobalt and the like, or mixtures thereof.

In some embodiments, the above process of preparing a compound of formula (III) further comprises conducting oxidation and deprotection of the compound of formula (III) to form the compound of formula (IV):

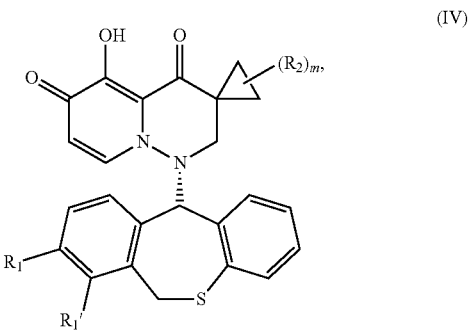

(IV)

or a salt thereof wherein $R_1$, $R_1'$, $R_2$, and m are as defined above; wherein the oxidation reaction is carried out in the presence of a first solvent and a oxidizing agent at a temperature between about 20° C. and about 60° C., such as 25° C. to 55° C., 30° C. to 50° C., 35° C. to 45° C., 40° C. to 45° C., 40° C. to 50° C., and 45° C. to 50° C.; and wherein the deprotection is carried out in the presence of a second solvent, a catalyst, and a suitable acid at a temperature between about 60° C. and about 100° C., such as 65° C. to 95° C., 70° C. to 90° C., 75° C. to 85° C., 75° C. to 80° C., or 80° C. to 85° C.

In at least one embodiment, the examples of the first solvent include, but are not limited to, toluene, THF, MTBE, DCM, diethyl ether, acetonitrile, acetone, dimethylcarbonate, ethylacetate, isopropylacetate, tertbutylacetate, $H_2O$, hexane, heptane and the like, or mixtures thereof.

In at least one embodiment, the examples of the oxidizing agent include, but are not limited to, Dess-Martin periodinane, manganese dioxide, 2-iodoxybenzoic acid, tetrapropylammonium perruthenate/N-methylmorpholine N-oxide (TPAP/NMO), pyridinium chlorochromate (PCC), pyridinium dichromate (PDC), sodium periodate, dimethylsulfoxide, sodium hypochlorite, Swern oxidation reagent and the like.

In at least one embodiment, the examples of the second solvent include, but are not limited to, toluene, THF, MTBE, DCM, diethyl ether, acetonitrile, acetone, dimethylcarbonate, dimethylacetamide, ethylacetate, isopropylacetate, tert-butylacetate, $H_2O$, hexane, heptane and the like, or mixtures thereof.

In at least one embodiment, the examples of the suitable acid include, but are not limited to, acetic acid, sulfuric acid, hydrochloric acid, hydrobromic acid, nitric acid, phosphoric acid, trifluoroacetic acid, maleic acid, fumaric acid, citric acid, oxalic acid, succinic acid, tartaric acid, malic acid, benzoic acid and the like, or mixtures thereof.

In at least one embodiment, the examples of the catalyst include, but are not limited to, lithium chloride, lithium bromide, lithium iodide, magnesium bromide, magnesium chloride, magnesium iodide, zinc chloride, tetra-n-butylammonium bromide, tetra-n-butylammonium chloride and the like, or mixtures thereof.

In some embodiments, the process of preparing a compound of formula (III) further comprises:

(1) conducting oxidation of the compound of formula (III) to form the compound of formula (III-a):

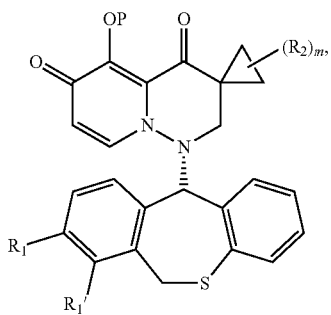

(III-a)

or a salt thereof in the presence of a first solvent and an oxidizing agent at a temperature between about 20° C. and about 60° C., such as 25° C. to 55° C., 30° C. to 50° C., 35° C. to 45° C., 40° C. to 50° C., 40° C. to 45° C., and 45° C. to 50° C.; and (2) deprotecting the compound of formula (III-a) to form the compound of formula (IV):

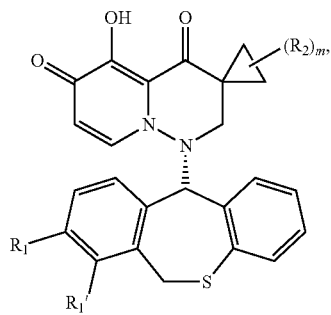

(IV)

or a salt thereof in the presence of a second solvent, a catalyst, and a suitable acid at a temperature between about 60° C. and about 100° C., such as 65° C. to 95° C., 70° C. to 90° C., 75° C. to 85° C., 80° C. to 85° C., and 75° C. to 80° C.; wherein $R_1$, $R_1'$, $R_2$, and m are as defined above.

In at least one embodiment, the examples of the first solvent include, but are not limited to, toluene, THF, MTBE, DCM, diethyl ether, acetonitrile, acetone, dimethylcarbonate, ethylacetate, isopropylacetate, tertbutylacetate, $H_2O$, hexane, heptane and the like, or mixtures thereof.

In at least one embodiment, the examples of the oxidizing agent include, but are not limited to, Dess-Martin periodinane, manganese dioxide, 2-iodoxybenzoic acid, tetrapropylammonium perruthenate/N-methylmorpholine N-oxide (TPAP/NMO), pyridinium chlorochromate (PCC), pyridinium dichromate (PDC), sodium periodate, dimethylsulfoxide, sodium hypochlorite, Swern oxidation reagent and the like.

In at least one embodiment, the examples of the second solvent include, but are not limited to, toluene, THF, MTBE, DCM, diethyl ether, acetonitrile, acetone, dimethylcarbonate, dimethylacetamide, ethylacetate, isopropylacetate, tertbutylacetate, $H_2O$, hexane, heptane and the like, or mixtures thereof.

In at least one embodiment, the examples of the suitable acid include, but are not limited to, acetic acid, sulfuric acid, hydrochloric acid, hydrobromic acid, nitric acid, phosphoric acid, trifluoroacetic acid, maleic acid, fumaric acid, citric acid, oxalic acid, succinic acid, tartaric acid, malic acid, benzoic acid and the like, or mixtures thereof.

In at least one embodiment, the examples of the catalyst include, but are not limited to, lithium chloride, lithium bromide, lithium iodide, magnesium bromide, magnesium chloride, magnesium iodide, zinc chloride, tetra-n-butylammonium bromide, tetra-n-butylammonium chloride and the like, or mixtures thereof.

In some embodiments, the compound of the present disclosure may be converted into a prodrug by any known methods. For example, the above process of preparing a compound of formula (IV) further comprises converting the compound of formula (IV) into a prodrug thereof having the following formula (V):

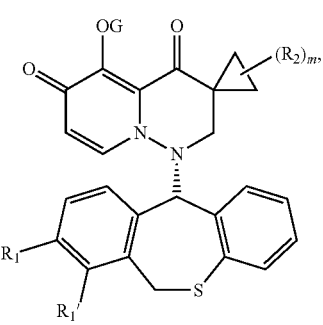

(V)

or a pharmaceutically acceptable salt thereof in the presence of an inert solvent, a suitable base and a catalyst at a temperature between about 30° C. and about 80° C., such as 35° C. to 75° C., 40° C. to 70° C., 45° C. to 65° C., 50° C. to 60° C., 50° C. to 55° C., and 55° C. to 60° C.; wherein $R_1$, $R_1'$, $R_2$, and m are as defined above; wherein G is any suitable prodrug group.

In at least one embodiment, the examples of the prodrug group include, but are not limited to,

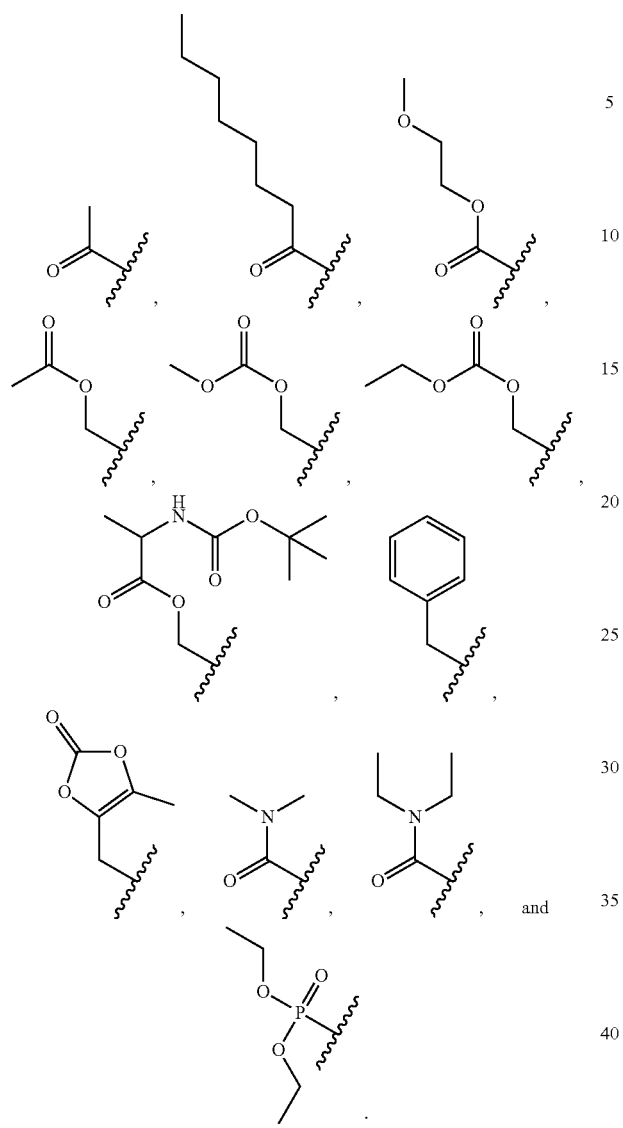

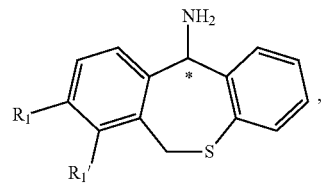

(I)

the process comprising: conducting a condensation of the compound of formula (I-1):

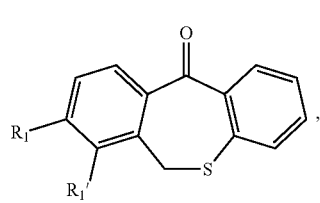

(I-1)

by contacting with a (R)-form or (S)-form chiral resolving agent, such as $C_{1-6}$ alkylsulfinamide and methylbenzylamine unsubstituted or substituted with one or more groups comprising halogen or $C_{1-3}$ alkyl, in the presence of a transition metal catalyst and an inert solvent; reducing with a suitable reducing agent, such as a borane reagent, in the presence of the inert solvent; and removing a protecting moiety, such as sulfinyl moiety and the ethylbenzene moiety, by treating with a mineral acid.

In at least one embodiment, the process of preparing a compound of formula (Ia):

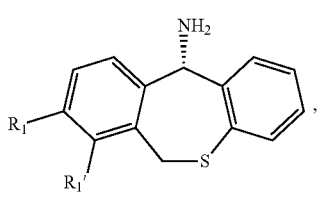

(Ia)

or a salt thereof comprises: conducting a condensation reaction of the compound of formula (I-1):

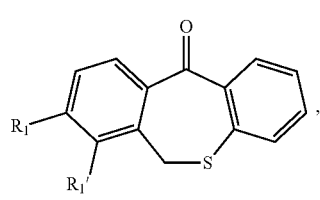

(I-1)

by contacting with a (S)—$C_{1-6}$ alkylsulfinamide or (S)-(−)-methylbenzylamine unsubstituted or substituted with one or more groups comprising halogen or $C_{1-3}$ alkyl in the presence of a transition metal catalyst and an inert solvent; reducing with a suitable reducing agent, such as a borane reagent, in the presence of the inert solvent at a temperature between about −30° C. and about 30° C., such as −25° C. to 25° C., −20° C. to 20° C., −15° C. to 15° C., −10° C. to 10°

In at least one embodiment, the examples of the inert solvent include, but are not limited to, toluene, THF, MTBE, DMA, diethyl ether, acetonitrile, acetone, dimethylcarbonate, ethylacetate, isopropylacetate, tertbutylacetate, $H_2O$, methanol, isopropanol, ethylene glycol, ethanol, propanol, hexane, heptane and the like, or mixtures thereof.

In at least one embodiment, the examples of the suitable base include, but are not limited to, an inorganic base, such as alkali metal hydroxides (e.g., sodium hydroxide, potassium hydroxide), alkali metal carbonates (e.g., sodium carbonate, potassium carbonate, $Cs_2CO_3$), alkali metal bicarbonates (e.g., sodium bicarbonate, potassium bicarbonate), alkali metal alkoxides (e.g., sodium methoxide, potassium methoxide) or an organic base and the like, or mixtures thereof.

In at least one embodiment, the examples of the catalyst include, but are not limited to, lithium iodide, sodium iodide, potassium iodide, lithium bromide, sodium bromide, potassium bromide, tetrabutyl ammonium bromide (TBAB) and the like, or mixtures thereof.

In another aspect of the present disclosure, a process of preparing the R-enantiomer or the S-enantiomer of the compound of formula (I) or a salt thereof is provided:

C., −10° C. to 5° C., −5° C. to 5° C., −5° C. to 0° C., and 0° C. to 5° C.; and removing the sulfinyl moiety or the ethylbenzene moiety by treating with a mineral acid; wherein $R_1$ is halogen, and $R_1'$ is halogen.

In at least one embodiment, the examples of the transition metal catalyst include, but are not limited to, titanium ethoxide, titanium methoxide, titanium isopropoxide, titanium tert-butoxide and the like.

In at least one embodiment, the examples of the borane reagent include, but are not limited to, $BH_3DMS$, $BH_3$-THF, BMS, $BH_3$-$Et_2NPH$ and the like.

In at least one embodiment, the examples of the inert solvent include, but are not limited to, toluene, THF, MTBE, DCM, diethyl ether, acetonitrile, ethylacetate, isopropylacetate, tertbutylacetate, $H_2O$, methanol, isopropanol, ethylene glycol, ethanol, propanol, hexane, heptane and the like, or mixtures thereof.

In at least one embodiment, the examples of the mineral acid include, but are not limited to, hydrochloric acid, orthophosphoric acid, trifluoracetic acid, acetic acid, trifluoromethane sulfonic acid, p-toluenesulfonic acid, methane sulfonic acid, nitric acid, sulfuric acid and the like, or mixtures thereof.

In some embodiments, the process of preparing a compound of formula (Ia):

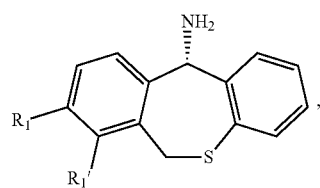
(Ia)

or a salt thereof comprises:

(1) conducting a condensation reaction by contacting the compound of formula (I-1):

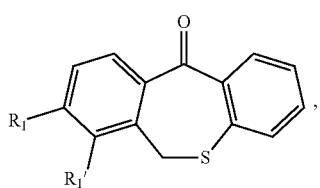
(I-1)

with a resolving agent, such as (S)—$C_{1-6}$ alkylsulfinamide or (S)-(−)-methylbenzylamine unsubstituted or substituted with one or more groups comprising halogen or $C_{1-3}$ alkyl, to form the compound of formula (I-1a) or (I-1b):

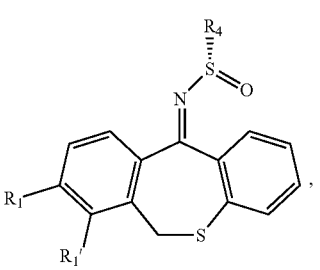
(I-1a)

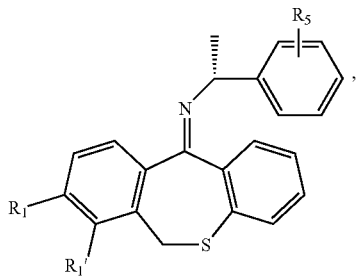
(I-1b)

or a salt thereof in the presence of a transition metal catalyst and a first solvent; wherein $R_1$ is halogen; $R_1'$ is halogen; $R_4$ is $C_{1-6}$ alkyl; and $R_5$ is halogen or $C_{1-3}$ alkyl; wherein the transition metal catalyst may be titanium ethoxide, titanium methoxide, titanium isopropoxide, titanium tert-butoxide and the like; wherein the first solvent may be toluene, THF, MTBE, DCM, diethyl ether, acetonitrile, ethylacetate, isopropylacetate, tertbutylacetate, $H_2O$, methanol, isopropanol, ethylene glycol, ethanol, propanol, hexane, heptane and the like, or mixtures thereof;

(2) reducing the compound of formula (I-1a) or (I-1b) with a suitable reducing reagent, such as a borane reagent, to form the compound of formula (I-1a-1) or (I-1b-1):

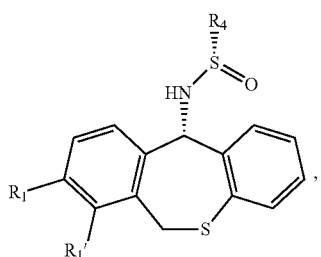
(I-1a-1)

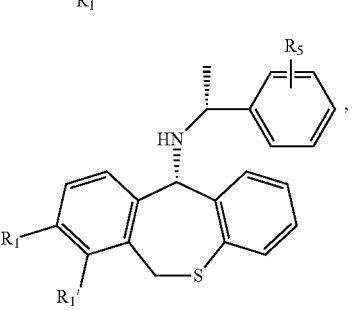
(I-1b-1)

or a salt thereof in the presence of a second solvent at a temperature between about −30° C. and about 30° C., such as −25° C. to 25° C., −20° C. to 20° C., −15° C. to 15° C., −10° C. to 10° C., −10° C. to 5° C., −5° C. to 5° C., −5° C. to 0° C., and 0° C. to 5° C.; wherein the reducing reagent may be $BH_3DMS$, $BH_3$-THF, BMS, $BH_3$-$Et_2NPH$ and the like; wherein the second solvent may be toluene, THF, MTBE, DCM, diethyl ether, acetonitrile, ethylacetate, isopropylacetate, tertbutylacetate, $H_2O$, methanol, isopropanol, ethylene glycol, ethanol, propanol, hexane, heptane and the like, or mixtures thereof; and (3) removing the sulfinyl moiety of the compound of formula (I-1a-1) by treating with a mineral acid; wherein the mineral acid may be hydrochloric acid, orthophosphoric acid, trifluoracetic acid, acetic acid, trifluoromethane sulfonic acid, p-toluenesulfonic acid, methane sulfonic acid, nitric acid, sulfuric acid and the like, or mixtures thereof; or removing the ethylbenzene moiety of the compound of formula (I-1b-1) by treating with a suitable reagent, such as a hydrogenating reagent.

In at least one embodiment, the process of preparing the compound of formula (IIa-1) further comprises the process of: preparing the compound of formula (Ia) by reacting the compound of formula (I-1) with a (S)—$C_{1-6}$ alkylsulfinamide, e.g., (S)-(–)-2-propanesulfinamide, in the presence of a transition metal catalyst and an inert solvent; reducing with a suitable reducing agent in the presence of an inert solvent; and removing the sulfinyl moiety by treating with a mineral acid.

Without further elaboration, it is believed that one skilled in the art can, based on the above descriptions, utilize the present disclosure to its fullest extent. The following examples are, therefore, to be construed as merely illustrative, and not limitative of the remainder of the disclosure in any way whatsoever. The publications cited herein are incorporated by reference in their entirety.

EXAMPLE

Example 1: Preparation of 2-methyl-propane-2-sulfinic acid (1,2-difluoro-11H-10-thia-dibenzo[a,d]cyclohepten-5-ylidene)-amide

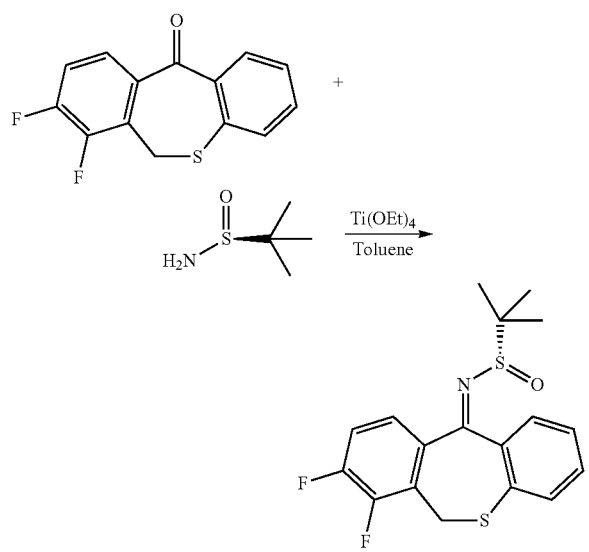

To a solution of 1,2-difluoro-11H-10-thia-dibenzo[a,d]cyclohepten-5-one (21 g, 80 mmole) and (S)-(–)-2-propanesulfinamide (11.6 g) in toluene was added Ti(OEt)$_4$ (titanium ethoxide, 65 g). The reaction mixture was stirred and heated to 55° C. for 5 hours under negative pressure. The reaction mixture was cooled down to room temperature, and ethylacetate (EA, 80 mL) was added, followed by adding 1 N HCl$_{(aq)}$ (hydrochloric acid, 250 mL), stirring for 10 minutes, then adding more EA (200 mL), and stirring for 3 minutes. The phases were separated, and the separated water phase was removed to give the organic phase. MgSO$_4$ (magnesium sulfate, 15 g) was added, followed by stirring for five minutes, filtered and concentrated. Next, EA (20 mL) was added and stirred. Then, heptane (200 mL) was added slowly, and solid was precipitated out. The mixture was stirred at room temperature for 4 hours and washed with heptane (50 mL) and dried to afford yellow solid product (25.5 g, 87.3% yield, >99% purity).

Example 2: Preparation of 2-methyl-propane-2-sulfinic acid (1,2-difluoro-5,11-dihydro-10-thia-dibenzo[a,d]cyclohepten-5-yl)-amide

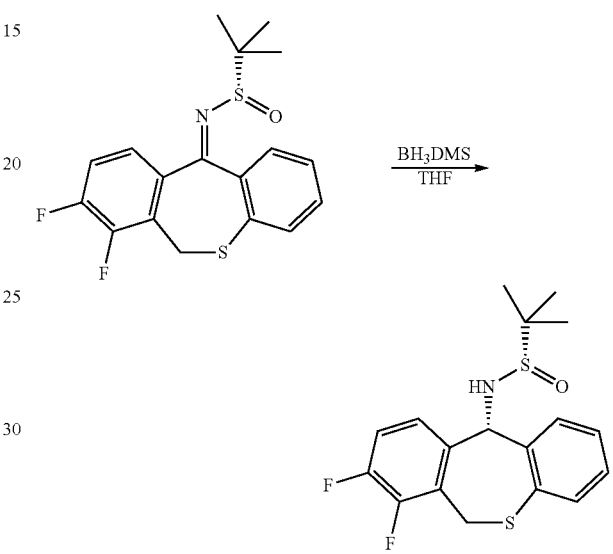

To a solution of 2-methyl-propane-2-sulfinic acid (1,2-difluoro-11H-10-thia-dibenzo[a,d]cyclohepten-5-ylidene)-amide (3.65 g, 10 mmole) was added anhydrate THF (tetrahydrofuran, 70 mL) and stirred. The reaction mixture was cooled down to –10° C. BH$_3$DMS (2 M) was added dropwise to the above THF solution, stirred for 2 hours at a temperature of –5° C. to 0° C. The end of the reaction was checked by HPLC. Methanol was added slowly, stirred for 30 minutes, followed by adding ice-saturated brine (250 mL, 0° C. to 5° C.) and EA (30 mL), stirred for 10 minutes, then subjected to separate and extract the organic phase. Further, more EA (20 mL) was added to the water phase, stirred for 5 minutes, then subjected to separate and extract the organic phase again. The extracted organic phases were combined. MgSO$_4$ (15 g) was added to remove water, and then filtered and concentrated, such that salt was formed. EA (50 mL) was added with stirring. The solution was filtered through a plate filter containing celite (15 g), and then concentrated. IPA (isopropyl alcohol, 7 mL) was added and heated until the solid was completely dissolved. Next, the solution was cooled down to room temperature, such that a solid was precipitated out. Hexane (50 mL) was added slowly, stirred at room temperature for 2 hours, filtered and washed with hexane (30 mL), dried to afford white solid product (2.3 g, 63% yield, >99% purity, e.e. value (S:R)>96%).

Example 3: Preparation of 1,2-difluoro-5,11-dihydro-10-thia-dibenzo[a,d]cyclohepten-5-ylamine

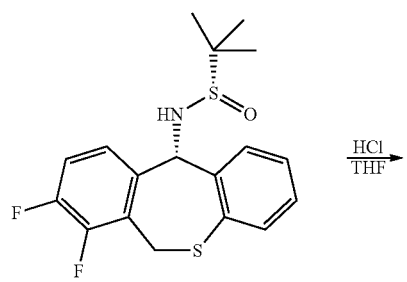

To a solution of 2-methyl-propane-2-sulfinic acid (1,2-difluoro-5,11-dihyro-10-thia-dibenzo[a,d]cyclohepten-5-yl)-amide (1.08 g, 2.94 mmole) in THF (5 mL) was added 4 N HCl in dioxane (3.5 mL) slowly. The ice bath was removed after the reagent was added completely. The reaction mixture was stirred at room temperature for 2 hours. The end of the reaction was checked by HPLC. The reaction mixture was cooled down to 0° C. to 5° C., and then 4 N sodium hydroxide (NaOH) was added slowly until the pH value become 11 to 12. EA (20 mL) was added, stirred for 5 minutes, and then subjected to separate and extract the organic phase. EA (10 mL) was further added to the water phase, stirred for 5 minutes, and subjected to separate and extract the organic phase again. The extracted organic phases were combined. MgSO$_4$ (3 g) was added, stirred to remove water, and then filtered, washed with EA (10 mL) and concentrated to dryness. EA (3 mL) was added, followed by adding heptane (30 mL) slowly, stirring for 1 hour, filtering, and drying to afford white solid product (0.658 g, 85% yield, >99% purity, e.e. value (S:R) >97%).

Example 4: Preparation of Compound (IIa-1-1)

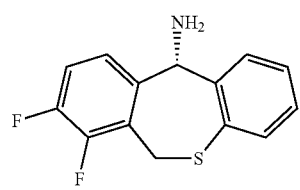

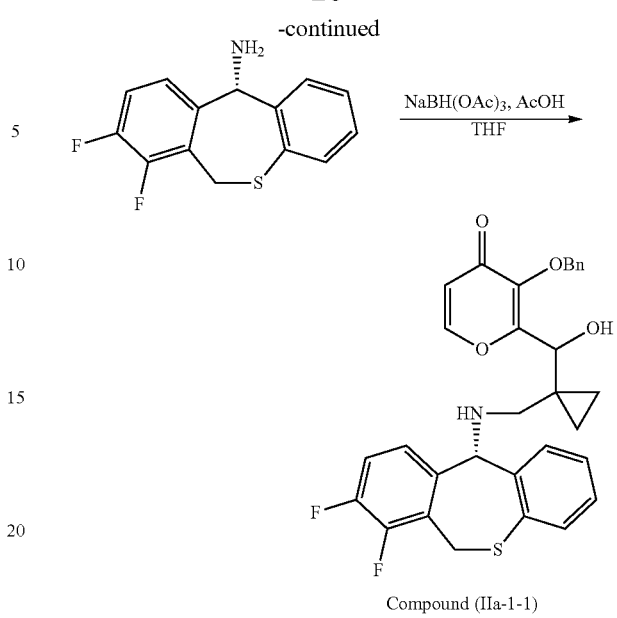

Compound (IIa-1-1)

1-((3-benxyloxy-4-oxo-4H-pyran-2-yl)-hydroxymethyl)-cyclopropanecarbaldehyde (360 g, 1.2 mole), 1,2-difluoro-5,11-dihydro-10-thia-dibenzo[a,d]cyclohepten-5-ylamine (263 g, 1 mole), THF (5 L) and acetic acid (90 mL) were added in a 10 L three-neck bottle. The reaction mixture was cooled down to 5±5° C. and stirred for 10 minutes. NaBH(OAc)$_3$ (sodium triacetoxyborohydride, 165 g/per 30 minutes, three times) was added, stirred for 2 hours at 5±5° C. After reaction completed, MeOH (methanol, 500 mL) was added, stirred for 10 minutes, followed by adding saturated brine (5 L) and EA (2 L), stirring for 10 minutes, and then subjecting to collect the EA layer. EA (1 L) was further added to the water phase, stirred for 5 minutes, and subjected to separate and remove the water phase. The collected phases were combined. MgSO$_4$ (150 g) was added, stirred for 10 minutes to remove water, and then filtered and concentrated to afford Compound (IIa-1-1), which was used for the next step without purification.

Example 5: Preparation of Compound (IIa-2-1)

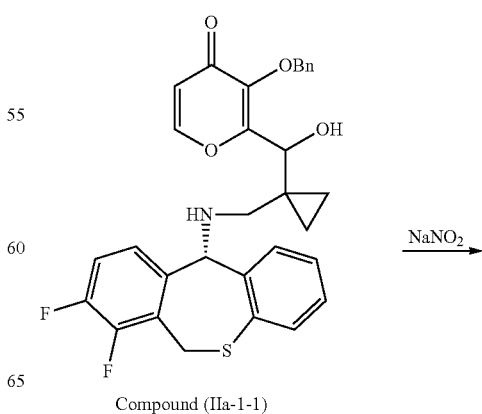

Compound (IIa-1-1)

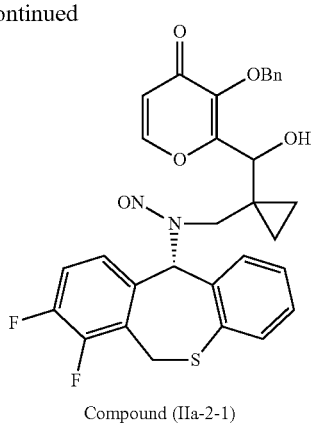

Compound (IIa-2-1)

The crude residue of the above step was stirred for 10 minutes in acetic acid (3.6 L) and H$_2$O (1 L) at 5±5° C., followed by adding NaNO$_2$ (sodium nitrite, 69 g/per 30 minutes, three times), stirring for 2 hours at 5° C. to 10° C. Ice H$_2$O was added, stirred for 30 minutes, filtered, and then washed with H$_2$O (1.5 L). EA (3 L) was added to dissolve the solid, followed by adding saturated brine (1.5 L), stirring for 10 minutes, and then subjecting to separate and remove the water phase. MgSO$_4$ (150 g) was added, stirred for 10 minutes to remove water, filtered, and then concentrated. IPA (500 mL) was added and heated to 50° C., and stirred for 10 minutes. Next, the reaction mixture was cooled down to 40° C., followed by adding hexane (3 L) slowly. After the reagent was added completely, the reaction mixture was stirred for 2 hours at room temperature, and then filtered, and dried to afford the Compound (IIa-2-1) (540 g, 93.7% yield, 99.28% purity).

Example 6: Preparation of Compound (III-1)

A solution of Zn (80 g) in THF (1.2 L), H$_2$O (800 mL) and AcOH (acetic acid, 100 mL) was stirred and heated to 60° C. Compound (IIa-2-1) (115 g) was dissolved in THF (300 mL), then added dropwise slowly to the above solution, and stirred for 2 hours at 60° C. The reaction mixture was cooled down to room temperature, filtered and adjusted for the pH to be between about 7 and 8 with 2 N NaOH, and then subjected to separate and collect the organic phase. EA (500 mL) was further added to the water phase, stirred for 5 minutes, and then subjected to separate and collect the organic phase again. The collected organic phases were combined. MgSO$_4$ (40 g) was added, stirred for 10 minutes at room temperature, filtered, washed with EA (100 mL), and then concentrated. EA (200 mL) was added, stirred, and heated to 50° C., and then solid was precipitated out. The reaction mixture was cooled down to room temperature after stirring 10 minutes, and then MTBE (methyl tert-butyl ether, 200 mL) was added, stirred for 30 minutes, followed by adding heptane (300 mL) slowly. After the reagent was added completely, the reaction mixture was stirred for 2 hours at room temperature, and then filtered, washed with MTBE/heptane (1:1, 100 mL, 0° C. to 5° C.), and vacuum dried (45° C. to 50° C.) to afford Compound (III-1) (52 g, 48% yield, 94% purity).

Example 7: Preparation of Compound (IV-1)

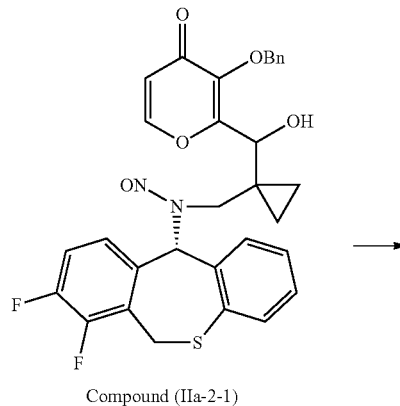

Compound (IIa-2-1)

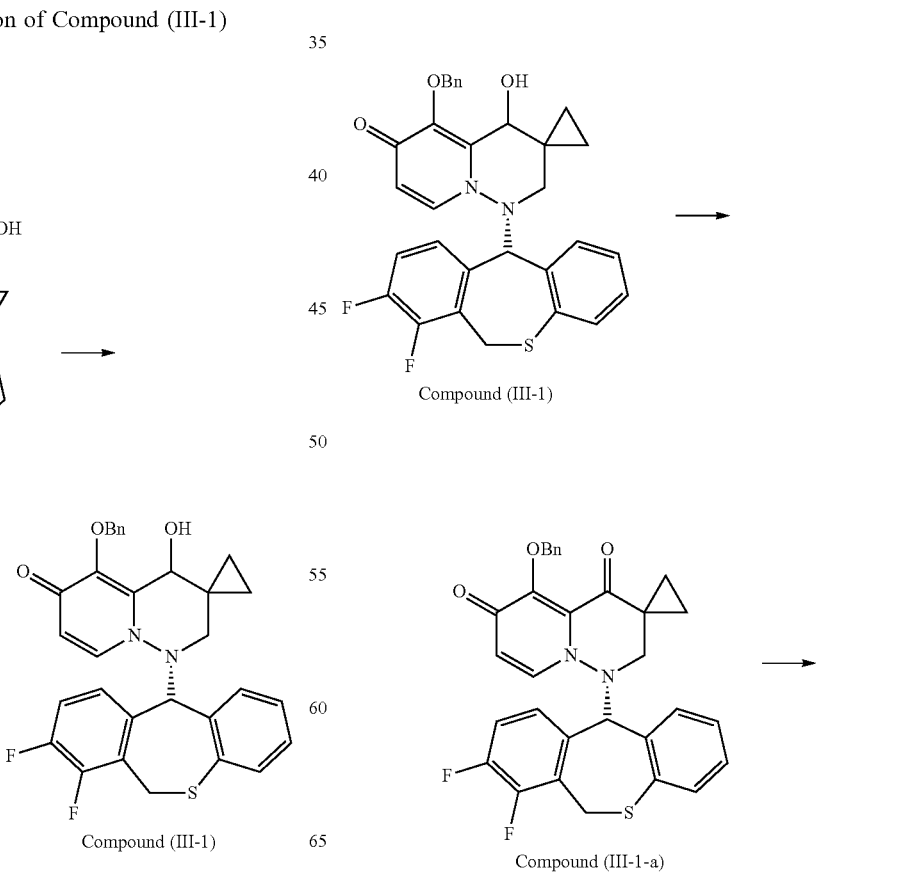

-continued

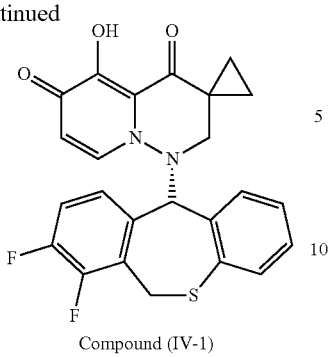

Compound (IV-1)

To a solution of Compound (III-1) (172 g, 320 mmole) in DCM (dichloromethane, 3.6 L) was added DMP (2,2-dimethoxypropane, 58 g). The reaction mixture was stirred and heated to about 40° C. for 1 hour, and then cooled down to 25° C. to 30° C. DMP (58 g) was added, heated to about 40° C., stirred for 1 hour, and then cooled down to 25° C. to 30° C. again. DMP (30 g) was added, heated to about 40° C., and stirred for 2 hours. The reaction mixture was cooled down to room temperature, filtered, washed with DCM (400 mL), and then added to $H_2O$ (4 L) under stirring. $NaHCO_3$ (sodium bicarbonate, 174 g) was added slowly, followed by adding $Na_2S_2O_3.5H_2O$ (sodium thiosulfate, 296 g), and stirring for 3 hours. Water phase was removed, and $MgSO_4$ was added, stirred for 10 minutes to remove water, and then filtered and concentrated to afford Compound (III-1-a), which was used for the next step without purification.

Compound (III-1-a) (133 g), LiCl (lithium chloride, 66.3 g), and DMA (dimethylacetamide, 520 mL) were added in a 3 L three-neck bottle, and stirred at 80° C. for 1 hour, then cooled down to 0° C. to 10° C., added with THF (700 mL), 0.5 N HCl (1.4 L), and stirred for 1 hour. DCM (1.4 L) was added, stirred for 5 minutes, extracted, and then washed with $H_2O$ (1.4 L) twice. $MgSO_4$ (80 g) and activated carbon (80 g) were added, stirred for 30 minutes, filtered, and concentrated to remove DCM and THF, and then solid was precipitated out. THF (200 mL) was added and stirred for 10 minutes, followed by adding MTBE (1.4 L), stirring for 2 hours at room temperature, filtering, washing with MTBE (230 mL), and then vacuum drying (40° C. to 45° C.) to afford Compound (IV-1) (115.8 g, 80% yield, 99% purity).

Other Embodiments

All of the features disclosed in this disclosure may be combined in any combination. Each feature disclosed in this disclosure may be replaced by an alternative feature serving the same, equivalent or similar purpose. Thus, unless expressly stated otherwise, each feature disclosed is only an example of a series of equivalent or similar features.

From the above descriptions, one skilled in the art can easily ascertain the characteristics of the present disclosure, and without departing from the scope thereof, can make various changes and modifications of the disclosure to adapt it to various usage and conditions. Thus, other embodiments are also within the scope of the following claims.

What is claimed is:

1. A compound represented by formula (I) below or a salt thereof,

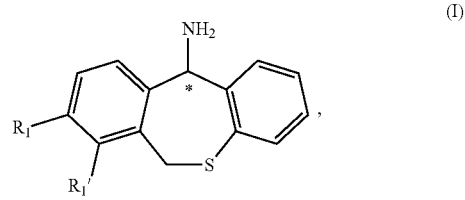

wherein $R_1$ is halogen; $R_1'$ is halogen; and "*" stands for an R-enantiomer or an S-enantiomer.

2. The compound or the salt thereof according to claim 1, wherein the compound is represented by formula (Ia) or formula (Ib) below:

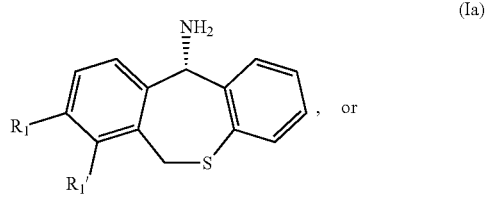

, or

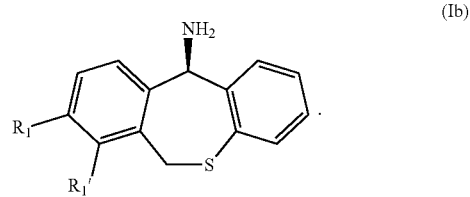

.

3. The compound or the salt thereof according to claim 2, which is

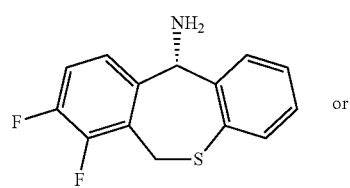

or

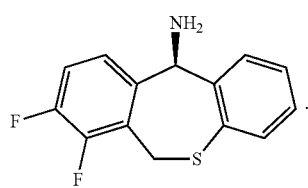

.

4. A compound represented by the formula (II) below or a salt thereof,

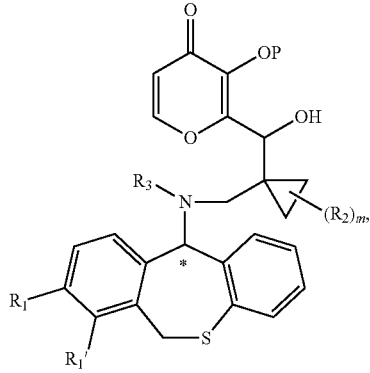

(II)

wherein $R_1$ is halogen; $R_1'$ is halogen; $R_2$ is hydrogen, deuterium, halogen, or $C_1$-$C_6$ alkyl; $R_3$ is hydrogen, NO, or $NH_2$; m is 0, 1, 2, or 3; P is a protecting group; and "*" stands for an R-enantiomer, an S-enantiomer or a racemate.

5. The compound or the salt thereof according to claim 4, wherein the compound is represented by formula (IIa) or formula (IIb) below:

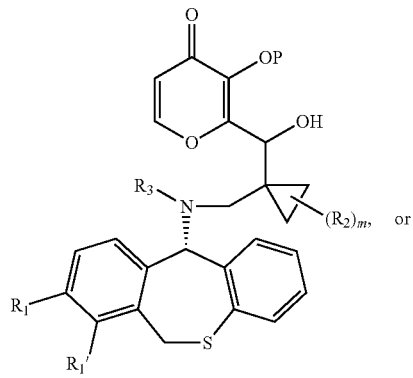

(IIa)

or

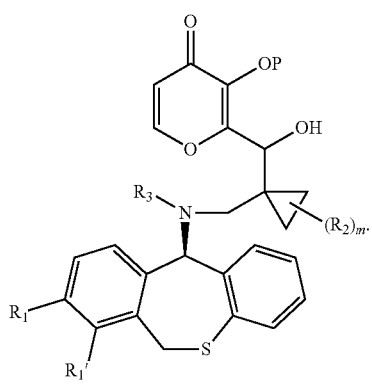

(IIb)

6. The compound or the salt thereof according to claim 5, wherein the compound is represented by formula (IIa-1), formula (IIa-2), formula (IIb-1), or formula (IIb-2) below:

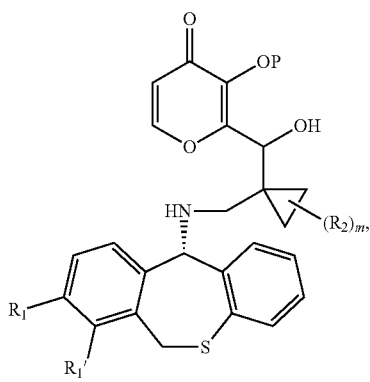

(IIa-1)

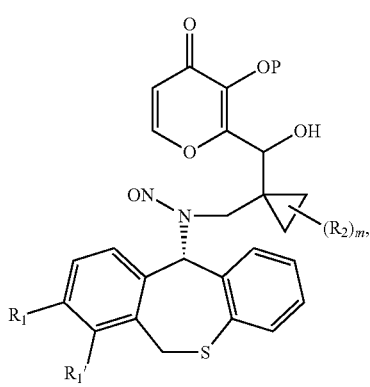

(IIa-2)

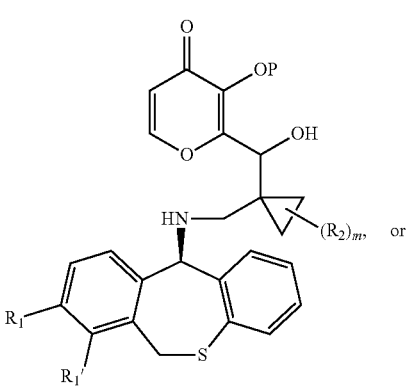

(IIb-1)

or

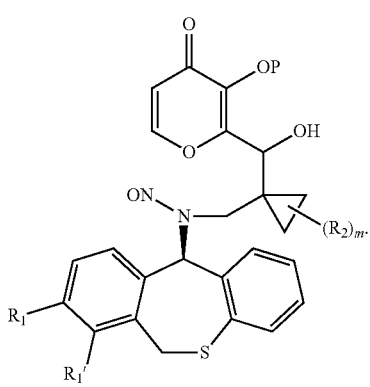

(IIb-2)

7. The compound or the salt thereof according to claim 6, which is

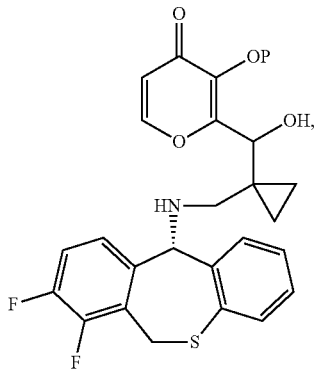

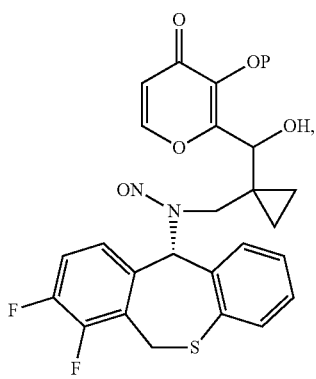

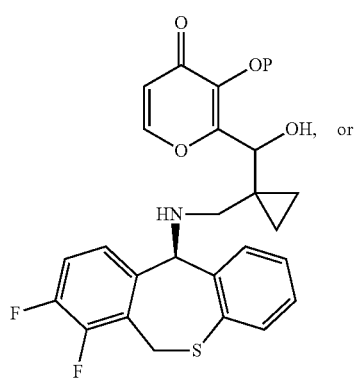

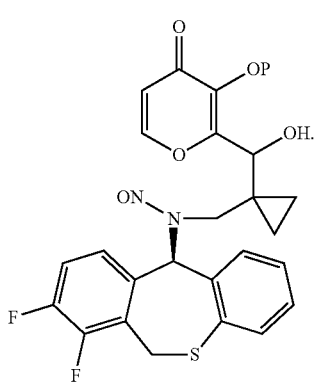

8. A process of preparing a compound of formula (Ia) below:

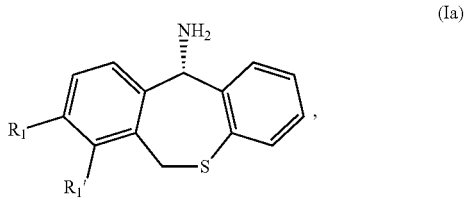

or a salt thereof, wherein $R_1$ is halogen, and $R_1'$ is halogen,
the process comprising conducting a condensation reaction by contacting a compound of formula (I-1) below:

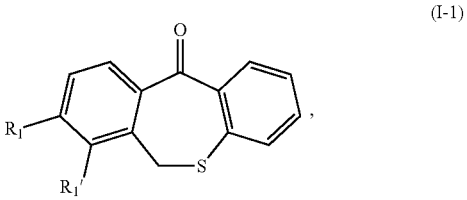

with (S)—$C_{1-6}$ alkylsulfinamide or (S)-(−)-methylbenzylamine unsubstituted or substituted with one or more groups comprising halogen or $C_{1-3}$ alkyl to form the compound of formula (Ia) or the salt thereof.

9. The process according to claim 8, further comprising a reduction step.

10. A process of preparing a compound of formula (IIa-1) below:

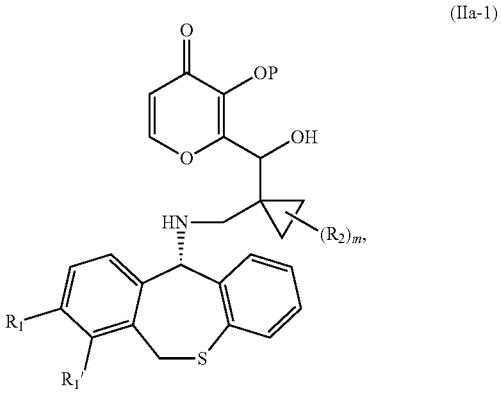

or a salt thereof, wherein $R_1$ is halogen; is halogen; $R_2$ is hydrogen, deuterium, halogen, or $C_1$-$C_6$ alkyl; m is an integer of 0, 1, 2, or 3; and P is a protecting group, the process comprising:
reacting a compound of formula (I-2) below with a compound of formula (Ia) below:

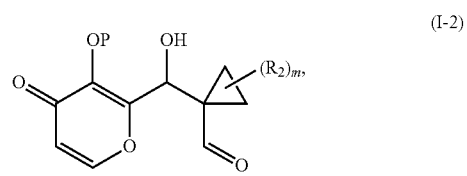

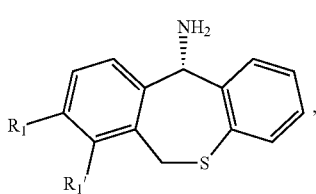

(Ia)

to form the compound of formula (IIa-1) or the salt thereof.

11. The process according to claim 10, further comprising conducting a condensation reaction by contacting a compound of formula (I-1) below:

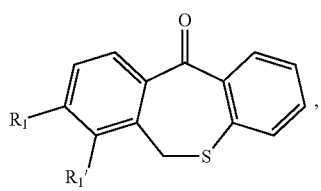

(I-1)

with (S)—C$_{1-6}$ alkylsulfinamide or (S)-(−)-methylbenzylamine unsubstituted or substituted with one or more groups comprising halogen or C$_{1-3}$ alkyl to form the compound of formula (Ia) or the salt thereof.

12. The process according to claim 10, further comprising subjecting the compound of formula (IIa-1) to nitrosation reaction to form a compound of formula (IIa-2) below:

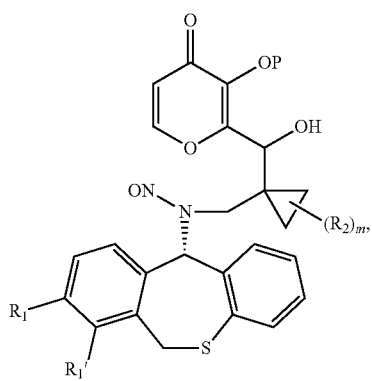

(IIa-2)

or a salt thereof.

13. The process according to claim 12, further comprising conducting a cyclization reaction of the compound of formula (IIa-2) to form a compound of formula (III) below:

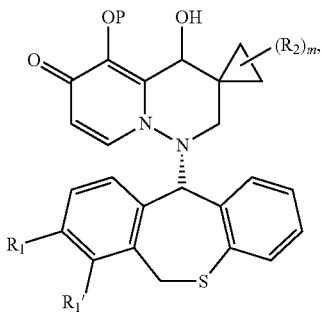

(III)

or a salt thereof.

14. The process according to claim 13, further comprising conducting oxidation and deprotection of the compound of formula (III) to form a compound of formula (IV) below:

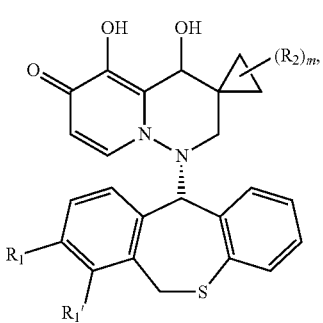

(IV)

or a salt thereof.

15. The process according to claim 14, further comprising converting the compound of formula (IV) into a prodrug, or a pharmaceutically acceptable salt thereof, represented by formula (V) below:

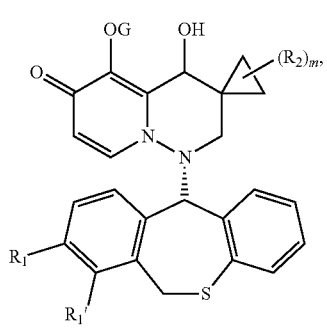

(V)

wherein G is a prodrug group.

* * * * *